United States Patent
Orwar et al.

(10) Patent No.: US 8,338,150 B2
(45) Date of Patent: *Dec. 25, 2012

(54) METHOD FOR COMBINED PARALLEL AGENT DELIVERY AND ELECTROPORATION FOR CELL STRUCTURES AN USE THEREOF

(75) Inventors: Owe Orwar, Hovás (SE); Mattias Karlsson, Onsala (SE); Kerstein Nolkrantz, Gothenburg (SE); Cecilia Farre, Västra Frolunda (SE)

(73) Assignee: Cellectricon AB, Gothenburg (SE)

( * ) Notice: Subject to any disclaimer, the term of this patent is extended or adjusted under 35 U.S.C. 154(b) by 1100 days.

This patent is subject to a terminal disclaimer.

(21) Appl. No.: 12/157,369

(22) Filed: Jun. 9, 2008

(65) Prior Publication Data

US 2009/0092963 A1    Apr. 9, 2009

Related U.S. Application Data

(63) Continuation of application No. 10/496,214, filed as application No. PCT/SE02/02192 on Nov. 27, 2002, now abandoned, which is a continuation of application No. 10/726,381, filed on Dec. 2, 2003, now Pat. No. 7,456,012, which is a continuation-in-part of application No. 10/325,691, filed on Dec. 19, 2002, now Pat. No. 7,109,034, which is a continuation of application No. 09/557,979, filed on Apr. 25, 2000, now Pat. No. 6,521,430, which is a continuation of application No. PCT/SE98/02012, filed on Nov. 6, 1998, which is a continuation-in-part of application No. 10/345,107, filed on Jan. 15, 2003, now Pat. No. 7,563,614.

(60) Provisional application No. 60/356,377, filed on Feb. 12, 2002.

(30) Foreign Application Priority Data

Nov. 6, 1997  (SE) ........................ 9704076
Nov. 27, 2001  (SE) ........................ 0103957

(51) Int. Cl.
C12N 13/00    (2006.01)

(52) U.S. Cl. .................. 435/173.6; 435/6.1; 435/173.4; 435/173.5; 435/285.2; 435/461; 800/25

(58) Field of Classification Search ............... 435/173.6, 435/173.4, 173.5, 397, 285.2; 600/373, 377, 600/378, 381, 395
See application file for complete search history.

(56) References Cited

U.S. PATENT DOCUMENTS

| | | | |
|---|---|---|---|
| 3,867,201 A | 2/1975 | Holmes | |
| 5,019,034 A | 5/1991 | Weaver et al. | |
| 5,035,139 A | 7/1991 | Hoefelmayr et al. | |
| 5,135,478 A | 8/1992 | Sibalis | |
| 5,137,817 A | 8/1992 | Busta et al. | |
| 5,208,145 A | 5/1993 | Rogers | |
| 5,389,069 A | 2/1995 | Weaver | |
| 5,449,492 A | 9/1995 | Krishtal | |
| 5,501,662 A | 3/1996 | Hofmann | |
| 5,597,699 A | 1/1997 | Lanzara | |
| 5,702,359 A | 12/1997 | Hofmann et al. | |
| 5,874,268 A | 2/1999 | Meyer | |
| 5,888,366 A * | 3/1999 | Engelhardt et al. | ........... 204/471 |
| 5,916,428 A | 6/1999 | Kane et al. | |
| 6,055,453 A | 4/2000 | Hofmann et al. | |
| 6,193,647 B1 | 2/2001 | Beebe et al. | |
| 6,208,893 B1 | 3/2001 | Hofmann | |
| 6,241,666 B1 | 6/2001 | Pomeranz et al. | |
| 6,261,815 B1 | 7/2001 | Meyer | |
| 6,278,895 B1 | 8/2001 | Bernard | |
| 6,283,951 B1 | 9/2001 | Flaherty et al. | |
| 6,326,177 B1 | 12/2001 | Schoenbach et al. | |
| 6,455,303 B1 | 9/2002 | Orwar et al. | |
| 6,470,226 B1 | 10/2002 | Olesen et al. | |
| 6,521,430 B1 | 2/2003 | Orwar et al. | |
| 7,018,819 B2 | 3/2006 | Orwar et al. | |
| 7,109,034 B2 | 9/2006 | Orwar et al. | |
| 2001/0029320 A1 | 10/2001 | Trumbull et al. | |

(Continued)

FOREIGN PATENT DOCUMENTS

EP    0 986 758 B1    12/1998

(Continued)

OTHER PUBLICATIONS

Kerstin Nolkrantz, et al.; "*Electroporation of Single Cells and tissues with an Electrolyte-filled Capillary*"; Analytical Chemistry; vol. 73; No. 18; Sep. 15, 2001; pp. 4469-4477.

(Continued)

*Primary Examiner* — Allison Ford
*Assistant Examiner* — Susan E Fernandez
(74) *Attorney, Agent, or Firm* — Edwards Wildman Palmer LLP; David G. Conlin

(57) ABSTRACT

Disclosed is a method for parallel delivery of agents to and/or into a cell structure, wherein at least two electrolyte-filled tubes are provided together with a counter electrode, the tubes being connected to a voltage or current generator, said agents being introduced into the electrolyte solution contained in the tubes, which are placed close to the cell structure, whereupon the agents are transported through the tubes to said cell structure and into the said structure through pores which have been formed by application of an electric field focused on the cell structure, resulting in electroporation of the cell structure. Also different applications of the method is disclosed, e.g. use of the method in order to transfer cell-impermeant solutes, such as drugs or genes, into the cell structure or out of the cell structure.

83 Claims, 10 Drawing Sheets

U.S. PATENT DOCUMENTS

| | | |
|---|---|---|
| 2002/0061589 A1 | 5/2002 | King et al. |
| 2002/0062126 A1 | 5/2002 | Lewis et al. |
| 2002/0063067 A1 | 5/2002 | Bech et al. |
| 2002/0074227 A1 | 6/2002 | Nisch et al. |
| 2002/0076689 A1 | 6/2002 | Farb et al. |
| 2002/0127723 A1 | 9/2002 | Palermo |
| 2002/0133137 A1 | 9/2002 | Hofmann |
| 2002/0146822 A1 | 10/2002 | Takayama et al. |
| 2002/0160437 A1 | 10/2002 | Meyer |
| 2002/0182627 A1 | 12/2002 | Wang et al. |
| 2002/0198485 A1 | 12/2002 | Dev et al. |
| 2002/0198512 A1 | 12/2002 | Seward |
| 2003/0009112 A1 | 1/2003 | Hammerle et al. |
| 2003/0009113 A1 | 1/2003 | Olson |
| 2003/0009148 A1 | 1/2003 | Hayakawa |
| 2003/0014081 A1 | 1/2003 | Bernabei |
| 2003/0017598 A1 | 1/2003 | Burke et al. |
| 2003/0022268 A1 | 1/2003 | Lepple-Wienhues |
| 2003/0153067 A1 | 8/2003 | Stett et al. |
| 2004/0029101 A1 | 2/2004 | Orwar et al. |
| 2004/0110307 A1 | 6/2004 | Karlsson et al. |
| 2004/0112529 A1 | 6/2004 | Karlsson et al. |
| 2004/0181343 A1 | 9/2004 | Wigstrom et al. |
| 2004/0182707 A1 | 9/2004 | Jardemark et al. |
| 2005/0009171 A1 | 1/2005 | Fertig et al. |
| 2005/0026283 A1 | 2/2005 | Ormar et al. |
| 2005/0048651 A1 | 3/2005 | Ryttsen et al. |
| 2006/0078961 A1 | 4/2006 | Chiu et al. |
| 2006/0223164 A1 | 10/2006 | Orwar et al. |
| 2006/0234298 A1 | 10/2006 | Chiu et al. |

FOREIGN PATENT DOCUMENTS

| | | |
|---|---|---|
| JP | 19950133907 | 5/1995 |
| WO | WO-90/04645 A1 | 5/1990 |
| WO | WO-94/20841 A1 | 9/1994 |
| WO | WO-95/23211 A1 | 8/1995 |
| WO | WO-96/00111 | 1/1996 |
| WO | WO-96/10170 A1 | 4/1996 |
| WO | WO-96/39226 A1 | 12/1996 |
| WO | WO-97/05922 A2 | 2/1997 |
| WO | WO-98/55870 A1 | 12/1998 |
| WO | WO-99/24110 A1 | 5/1999 |
| WO | WO-00/34434 | 6/2000 |
| WO | WO-01/07583 A1 | 2/2001 |
| WO | WO-01/09297 A1 | 2/2001 |
| WO | WO-01/43817 A1 | 6/2001 |
| WO | WO-01/48180 A2 | 7/2001 |
| WO | WO-01/94939 A1 | 12/2001 |
| WO | WO-02/31171 A2 | 4/2002 |
| WO | WO-02/33066 A1 | 4/2002 |
| WO | WO02/100459 | 12/2002 |
| WO | WO-03/013647 A2 | 2/2003 |
| WO | WO-03/046170 A1 | 6/2003 |
| WO | WO-03/046171 A1 | 6/2003 |
| WO | WO-03/068906 A1 | 8/2003 |
| WO | WO-2004/039489 A2 | 5/2004 |
| WO | WO-2006/74350 A2 | 7/2006 |

OTHER PUBLICATIONS

Devin V. McAllister, et al.; "*Microfabricated Microneedles for Gene and Drug Delivery*"; Annu. Rev. Biomed. Eng.; 2000; 02; pp. 289-313.

Aberg et al., "Selective Introduction of Antisense Oligonucleotides into Single Adult CNS Progenitor Cells Using Electroporation Demonstrates the Requirement of Stat3 Activation for CNTF-Induced Gliogenesis", *Molecular and Cellular Neuroscience* 17, 426-443 (2001).

Capecchi, "High efficiency transformation by direct microinjection of DNA into cultured mammalian cells" *Cell*, 22, 479-488 (1980).

Chang, "Cell poration and cell fusion using an oscillating electric field." *J. Biophys.*, 56, 641-652 (1989).

Chow et al., "Delay in vesicle fusion revealed by electrochemical monitoring of single secretory events in adrenal chromaffin cells" *Nature*, 356, 60-63 (1992).

Collombet et al., "Introduction of Plasmid DNA into Isolated Mitochondria by Electroporation: A Novel Approach Toward Gene Correction for Mitochondrial Disorders" *J. Biol. Chem.*, 272, 5342-5347 (1997).

Farre et al., "Screening of Ion Channel Receptor Agonists Using Capillary Electrophoresis-Patch Clamp Detection with Resensitized Detector Cells", *Anal. Chem.* 2001, 73, 1228-1233.

Fertig et al., "Whole Cell Patch Clamp Recording Performed on Planar Glass Chip", *Biophysical Journal*, vol. 82, Jun. 2002, 3056-3062.

Fishman et al., "Cell-to-Cell Scanning in Capillary Electrophoresis", *Analytical Chemistry*, vol. 68 No. 7, Apr. 1, 1996, 1181-1186.

Fishman et al., "Identification of receptor ligands and receptor subtypes using antagonists in a capillary electrophoresis single-cell biosensor separation system", *Proc. Natl. Acad. Sci. USA*, vol. 92, pp. 7877-7881, Aug. 1995.

Hamill et al., "Improved Patch-Clamp Techniques for High-Resolution Current Recording from Cells and Cell-Free Membrane Patches", *Pflugers Archiv* (1981) 391:85-100.

Hibino et al., "Membrane conductance of an electroporated cell analyzed by submicrosecond imaging of transmembrane potential" *Biophys. J.*, 59, 209-220 (1991).

Jardemark et al., "Screening of Receptor Antagonists Using Agonist-Activated Patch Clamp Detection in Chemical Separations", *Anal. Chem.* 1998, 70, 2468-2474.

Jaroszeski et al., "Electrochemotherapy: an emerging drug delivery method for the treatment of cancer," *Advanced Drug Delivery Review*, vol. 26, (1997), pp. 185-197.

Jorgenson et al., "Zone electrophoresis in Open-Tubular Glass Capillaries", *Anal. Chem.* 53, 1298-1302 (1981).

Karlsson et al., "Electroinjection of Colloid Particles and Biopolymers into Single Unilamellar Liposomes and Cells for Bioanalytical Applications", *Anal. Chem.*, 72, 5857-5862 (2001).

Kinosita et al., "Electroporation of cell membrane visualized under a pulsed-laser fluorescence microscope" J. *Biophys.*, 53, 1015-1019 (1988).

Kinosita et al., "Voltage-induced conductance in human erythrocyte membranes" *Biochim. Biophys. Acta*, 554, 479-497 (1979).

Klemic et al., "Micromolded PDMS planar electrode allows patch clamp electrical recordings from cells", *Biosensors and Bioelectronics* 17 (2002) 597-604.

Lundqvist et al., "Altering the biochemical state of individual cultured cells and organelles with ultramicroelectrodes", *Proc. Natl. Acad. Sci.* 95, 10356-10360 (1998).

Maiti et al., "Measuring Serotonin Distribution in Live Cells with Three-Photon Excitation" *Science*, 275, 530-532 (1997).

Marszalek et al., "Kinetics of Release of Serotonin from Isolated Secretory Granules, I. Amperometric Detection of Serotonin from Electroporated Granules", *Biophysical Journal*, vol. 73 (Sep. 1997) pp. 1160-1168.

Mir et al., "L'electrochimiotherapie, un nouveau traitement antitumoral: prelier essai clinique," *C R Acad Sci. III*, 1991, 313, 613-618 (article is in French, with Abridged English Version).

Needham, "Measurement of interbilayer adhesion energies", 1993, *Methods in Enzymology* vol. 220, pp. 111-129.

Okino et al., "Effects of a high-voltage electrical impulse and an anticancer drug on in vivo growing tumors," *Jpn J. Cancer Res.*, vol. 78, pp. 1319-1321, Dec. 1987.

Orwar et al., "Patch-Clamp Detection of Neurotransmitters in Capillary Electrophoresis", *Science*, vol. 272, Jun. 21, 1996, 1779-1782.

Ramirez et al., "Electrochemotherapy on liver tumours in rabbits," *Br. J. Cancer*, 1998, 77, 2104-11.

Ryttsen et al., "Characterization of Single-Cell Electroporation by Using Patch-Clamp and Fluorescence Microscopy", *Biophysical Journal* 79, 1993-2001 (2000).

Salford et al., "A new brain Tumour therapy combining bleomycin with in vivo electropermeabilication," *Biochem. Biophys. Res. Commun.*, 1993, 194, 938-43.

Sinclair et al. "A Cell-Based Bar Code Reader for High-Throughput Screening of Ion Channel-Ligand Interactions", *Anal. Chem.* 2002, 74,6133-6138.

Stromberg et al., "Microfluidic Device for Combinatorial Fusion of Liposomes and Cells", *Anal Chem.* 2001, 73, 126-130.

Swartz et al., "Sparking New Frontiers: Using in Vivo Electroporation for Genetic Manipulations" *Development Biology* 233, 13-21 (2001).

Templeton et al., "Efficient gene targeting in mouse embryonic stem cells," *Gene Therapy* (1997), vol. 4, pp. 700-709.

Teruel et al., Electroporation-Induced Formation of Individual Calcium Entry Sites in the Cell Body and Processes of Adherent Cells *Biophys. J.*, 73, 1785-1796 (1997).

Tsong, "Electroporation of cell membranes," *Biophysical Society*, vol. 60, 1991 (297-306).

Weaver, "Electroporation: A general phenomenon for manipulating cells and tissues," *J. Cell. Biochem.*, vol. 51, 426-435 (1993).

Wightman et al., "Temporally resolved catecholamine spikes correspond to single vesicle release from individual chromaffin cells" *Proc. Natl. Acad. Sic. U.S.A.*, 88, 10754-10758 (1991).

Zheng et al., "High-efficiency gene transfection by in situ electroporation of cultured cells" *Biochim. Biophys. Acta*, 1088, 104-110 (1991).

Zimmerman, "Electric field-mediated fusion and related electrical phenomena," *Biochim. Biophys. Acta*, 694, 227-277 (1982).

International Search Report in PCT/SE98/02012 dated Feb. 18, 1999.

International Search Report in PCT/SE02/02192 dated Feb. 28, 2003.

\* cited by examiner

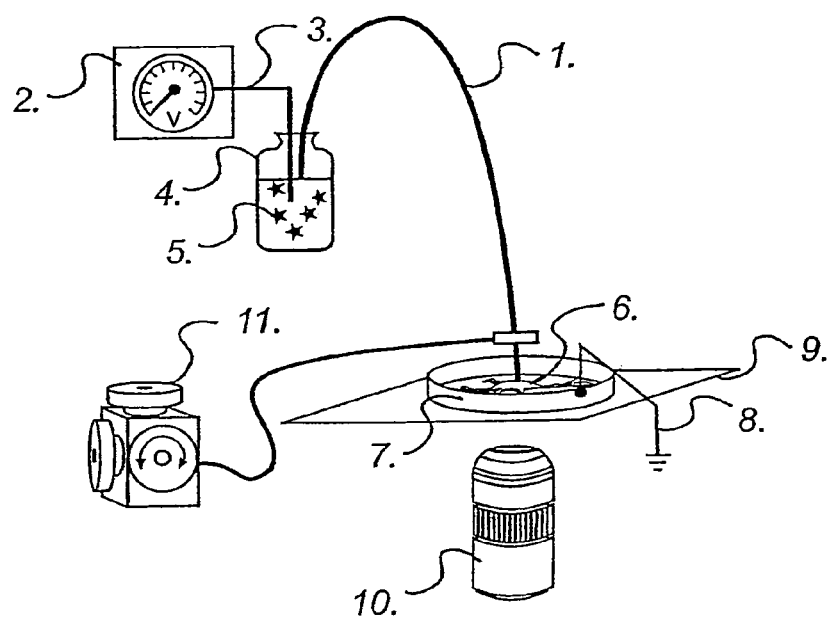
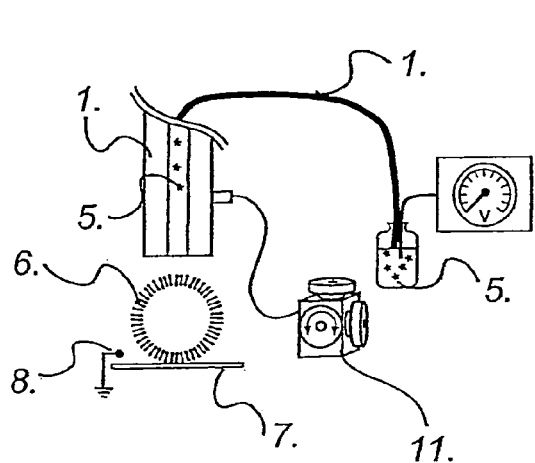 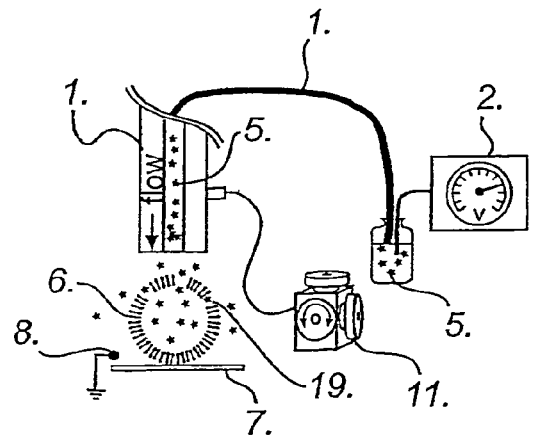
Fig. 1a.
Fig. 1b.          Fig. 1c.

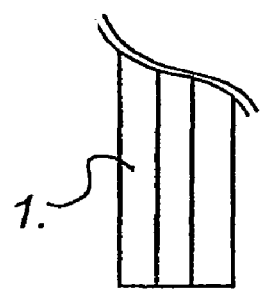 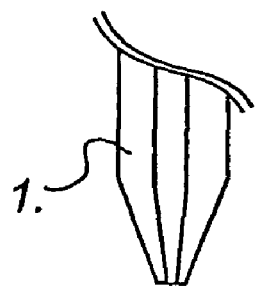 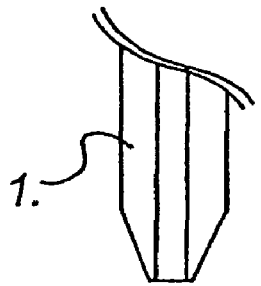
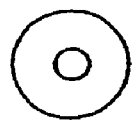 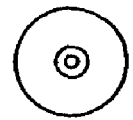 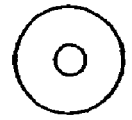
Fig. 2a.  Fig. 2b.  Fig. 2c.
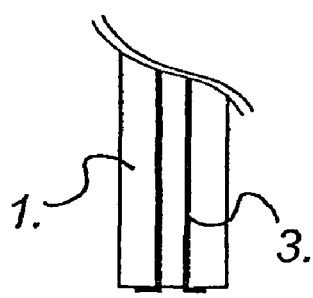 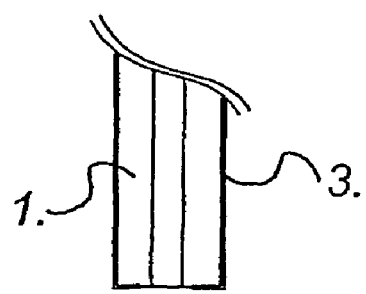
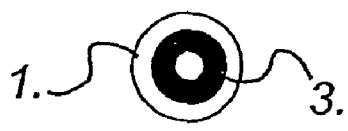 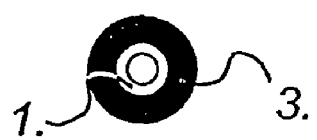
Fig 2d.  Fig 2e.

METHOD FOR COMBINED PARALLEL AGENT DELIVERY AND ELECTROPORATION FOR CELL STRUCTURES AN USE THEREOF

RELATED APPLICATION(S)

This application is a continuation of application Ser. No. 10/496,214, filed May 20, 2004, which is the U.S. National stage of International Application No. PCT/SE02/02192, filed on Nov. 27, 2002, which claims the benefit of Swedish Application No. 0103957-7, filed on Nov. 27, 2001. This application is also a continuation-in-part of application Ser. No. 10/726,381, filed Dec. 2, 2003, which is a continuation-in-part of application Ser. No. 10/325,691, (now U.S. Pat. No. 7,109,034) filed Dec. 19, 2002, which is a continuation of application Ser. No. 09/557,979 (now U.S. Pat. No. 6,521,430) filed Apr. 25, 2000, which is a continuation of International Application No. PCT/SE98/02012, filed Nov. 6, 1998, which claims priority to Swedish Application No. 9704076-0, filed Nov. 6, 1997 and is also a continuation-in-part of application Ser. No. 10/345,107, filed Jan. 15, 2003, which claims priority to U.S. Provisional Application No. 60/356,377, filed Feb. 12, 2002.

FIELD OF THE INVENTION

The present invention relates to a highly spatially resolved method for the electroporation and parallel delivery of one or several different compounds into cell structures, such as cells, cell-like structures, or a population of cells. Preferably, at least two electrolyte-filled capillaries (EFCs), a linear array of EFCs, or a two-dimensional matrix array of EFCs coupled to a voltage generator are used as a combined electroporation and delivery tool of, for example, multiple dyes, drugs, DNA, RNA, antisense oligonucleotides and biomolecules into the cytoplasm of single cells or populations of cells in a sequential or parallel manner or combinations thereof. The invention also relates to the use of these methods. In particular, it relates to methods for rapid screening of drugs that affect intracellular chemistry, and for the identification and detection of intracellular proteins.

BACKGROUND OF THE INVENTION

Fast and reliable methods for investigating drug actions on intracellular chemistry are in high demand today. Such protocols could include screening for ligands and substrates that interact with organelle-bound receptors and cytosolic enzymes, respectively. Also methods that allow for characterization and detection of all proteins inside cells would be extremely valuable, not the least in the area of proteomics. Highly specific enzymes substrates and protein probes are available that makes it possible to detect particular components in cells. (Tsien R Y, Annu. Rev. Biochem. 1998, 67, 509-44). For example, there are a variety of substrates available that can be employed as light switches in the substrate-product conversion step. Also, specific protein-protein interactions can be identified by the use of a fluorescence indicator coupled to protein splicing (Ozawa T, Nogami S, Sato M, Ohya Y, Umezawa Y, Anal. Chem. 2000, 72, 5151-57). Although these probes and indicators are available, the main challenge so far in applying these probes and indicators is to introduce them into the cellular interior. Many of these probes and indicators as well as many other compounds for biological and medical use including drugs and biomolecules that are of interest to include in cells are polar. Polar solutes are cell-impermeant and unable to pass biological membranes.

Furthermore, methods that allow for the detection of DNA-protein, protein-protein and many more interactions inside cells would be a valuable tool in many areas. Likewise, the ability to introduce viruses, bacteria, antibodies, and colloidal particles to cells is judged to be of importance in many areas of the biosciences. It is, however, difficult to transfer all these compounds and particles to the cytosol of a cell owing to the presence of a cell plasma membrane barrier, which acts as a physical boundary to the external solution that prevents the entrance of exogenous compounds and particles.

It has for a long time been recognized that cell membranes can be permeabilized by pulsed electric fields (see e.g. Zimmermann, U. *Biochim. Biophys Acta,* 694, 227-277 (1982). This technique is called electroporation. It is known from work on electrochemical detection in capillary electrophoresis (CE) that the voltage applied over an electrolyte filled capillary (EFC) will create an electric field at the capillary outlet (Lu, W.; Cassidy, M. *Anal. Chem.* 1994, 66, 200-204). This electric field at the tip of an EFC working against ground potential can be used for electroporation. The same EFC that performs the electroporation also delivers the agents of interest to the cell. It can be shown that the magnitude of the electric field along the axis of symmetry of the EFC lumen, extending out into solution is given by:

$$E(Z, \Psi) = \frac{\Psi}{L_c}\left[\frac{Z}{[1+(Z)^2]^{\frac{1}{2}}} - 1\right] \quad (1)$$

Where Z is the dimensionless distance from the tip of the EFC, z/a, where z is distance from the EFC tip and a is the EFC lumen radius. $\Psi$ is the applied potential in volts and $L_c$ is the length of the EFC. This equation can be integrated to find the potential drop along the cylindrical axis outside the capillary.

$$V(Z) = \frac{a\Psi}{L_c}\left((Z^2+1)^{1/2} - Z\right) \quad (2)$$

The transmembrane voltage can thus be approximated from this field by using equation (2) as described above.

The inventors have previously demonstrated the concept of electroporation using a singular EFC containing a homogeneous electrolyte solution (K. Nolkrantz, R. I. D. Karlsson, C. Farre, A. Brederlau, C. Brennan, P. S. Eriksson, S. G. Weber, M. Sandberg, O. Orwar Anal. Chem., (2001) 73, 4469-4477; WO 9924110).

SUMMARY OF THE INVENTION

What is disclosed here are substantial improvements in the technology that allows for rapid parallel delivery, which can be performed together with sequential delivery in a combinatorial way, of one or more agents, such as internalizing agents, to and into one or more cell structures using two, or preferably a plurality of, EFCs. The present invention also relates to several applications of the technology.

The present invention relates to a highly spatially resolved technique enabling rapid screening of drugs that affect intracellular chemistry, and for the identification and detection of intracellular proteins, and is based on the permeabilization of phospholipid bilayer membranes by electric fields, i.e. so called electroporation.

Rapid intracellular delivery of multiple cell-impermeable agents is achieved based on the use of at least two EFCs supplemented with cell-loading agents. A voltage or current, such as a voltage or current pulse, applied across an EFC gives rise to a electric field outside the terminus of the EFC thus causing pore formation in cellular membranes. In addition, this voltage or current may, for example, induce an electroosmotic flow of electrolyte contained in the EFC. As the EFC is supplemented with cell-loading agents, the electroosmotic flow delivers these agents at the site of pore formation. The combination of pore formation and delivery of agents supplemented to the EFC electrolyte enables loading of materials into, for example, the cytoplasm or organelles. Disclosed here is a method for parallel delivery, which may be performed together with parallel delivery in a combinatorial way, of one or multiple loading agents into a cell structure, such as to the cytosol of a cell or a population of cells or a similar structure based on the EFC electroporation protocol.

The method according to the present invention can be used as a screening technique for intracellular drug actions and as a technique for the identification of intracellular proteins inside cells. Example of such proteins can be enzymes, receptors, or structural proteins. In these instances, the electroporation technique is used for the introduction of one or several protein probes (e.g. fluorogenic ligands or substrates) into single cells or populations of cells. These markers can be introduced in combination with drugs, substrates or ligands that interact directly with the target protein or proteins in the same signaling pathways. Thus both the presence of various proteins and their function can be obtained on the single cell level. Tools with such capabilities might be suited both for proteomics, and phenotype profiling, as well as for characterizing the action of drugs on intracellular signaling systems or metabolic pathways. In addition, the method according to the invention can be used to identify receptor ligands and enzymes substrates in biosensor-chemical separation formats. To use the invention for profiling, screening and probing of e.g. intracellular proteins or drug actions inside living cells it is required that events related to these interactions can be detected. This can be achieved by, for example, the use of selective fluorescent protein markers in combination with fluorescence microscopy. As an example, to verify the presence of a certain enzyme inside a cell a polar cell-membrane-impermeant substrate that is non-fluorescent but after enzymatic conversion it is converted into a fluorescent product. Then an increase in fluorescence would reflect the presence of the enzyme in the cell as well as the enzymatic activity. The protein marker (fluorogenic substrate) is introduced into the cytosol of a living cell using the disclosed electroporation technique. The marker can also be introduced together with a drug or an inhibitor.

Thus, the present invention relates to a method for alteration of a biochemical content of cell structure. More precisely, the present invention relates to a method for parallel delivery of agents to a surface of a cell structure and into the cytoplasm of the cell structure, comprising the following steps:

(a) at least two electrolyte-filled tubes are provided together with a ground or counter electrode, (b) the electrolyte-filled tubes are connected to a voltage or current generator, (c) at least one agent is introduced into the electrolyte solution contained in each electrolyte-filled tube, (d) the electrolyte-filled tubes are placed at close distance to the surface of a cell structure, (e) the agent(s) is/are transported through the electrolyte-filled tubes to the surface of the cell structure, (f) an electric field of a strength sufficient to obtain electroporation of the surface of the cell structure is focused on the cell structure, resulting in formation of pores in the membrane surface of the cell structure, and (g) the agent(s) is/are transported through the pores formed in step (f) and into the cytoplasm of the cell structure, wherein steps (a-g) are performed in consecutive order, with the exception that the order of steps (b), (c) and (d) may be altered, and that the order of steps (e) and (f) may be altered.

According to step (a) above, a ground or counter electrode is used. It is possible to use only one such ground or counter electrode, or more than one ground or counter electrodes such as one ground or counter electrode for each electrolyte-filled tube.

According to step (b) above, a voltage or current generator is used. It is possible to use only one such a voltage or current generator, or more than one a voltage or current generator.

The expression "at close distance", used in step (d) above, means that the outlet end of the capillary is placed in contact with or very near the cell structure. Preferably, said close distance is less than 500 μm.

The expression "an electric field of a strength sufficient to obtain electroporation is focused on the cell structure", used in step (f) above, means that an electric field is focused on or over the cell structure or the part of the cell structure that is to be electroporated, and that this electrical field is essentially exactly what is needed for electroporation. Preferably, the voltage generator generates a voltage that is from 10 mV to 100 V at the surface of the cell structure to be electroporated, and more preferably it is from 100 mV to 2 V at said surface. The voltage pulse is preferably from 0.1 μs to several minutes. By several is here intended e.g. 1-10 minutes. More preferably the voltage pulse is from 1 μs to 5 s, and most preferably it is less than 100 ms.

In step (g) agent is transported into the cell structure. Either is all the amount of the agent delivered from the electrolyte-filled tube to the surface of the cell structure transported further into the cell structure, or is only a part of this amount is transported further into the cell structure with the other part remaining outside the cell surface.

The cell structure can be any kind of cell or cell-like structure, such as a cell in a primary cell culture, a cell in a tissue slice or a tissue, an in vivo cell, a liposome, or an intracellular cell structure, such as an organelle, as discussed further below.

The electrolyte-filled tubes may be electrolyte-filled capillaries (EFCs), electrolyte-filled conically tapered tubes, and/or electrolyte-filled electrodes. These expressions are used interchangeably throughout this specification.

By using parallel delivery, it is possible to deliver agents either through pores formed in one cell structure or through pores formed in two or more different cell structures.

Furthermore, it is possible to place more than one agent in each electrolyte-filled tube. This makes it possible to combine the parallel delivery of agent into the cell structure with sequential delivery of agent into the cell structure in a combinatorial manner.

The method according to the invention may be used for transferring multiple solutes, agents, and particles into a permeabilized cell structure.

BRIEF DESCRIPTION OF THE DRAWINGS

In the description and the examples below reference is made to the accompanying drawings, on which:

FIG. 1 shows an appropriate apparatus for electroporation of cells and cellular structures using the method according to the present invention. One embodiment is illustrated in FIG. 1a, comprising one EFC 1, connected to a voltage generator 2 via a first electrode 3 and a vial 4, containing an electrolyte solution of same composition as inside said EFC. This electrolyte solution is supplemented with an agent 5, to be introduced to the cellular structure. The cell structure 6 is held in physiological buffer in e.g. a petri dish 7 preferably equipped with a ground bath-type counter electrode 8. In the preferred embodiment shown here, the petri dish is situated on an inverted microscope stage 9, and viewed through a microscope objective 10 in order to facilitate positioning of the EFC tips in relation to the cell structure. The EFC is, by means of a three-dimensional micropositioner 11, positioned close to the cell structure. This is performed in such a way that the electric field produced between the electrodes is highly focused over the structure to be electroporated. FIG. 1b and FIG. 1c illustrate how the embodiment of FIG. 1a can be used for loading a cell structure 6 with a cell-impermeable agent 5. In FIG. 1b, the EFC 1 containing the cell-impermeable agent 5, is positioned by the use of a micropositioner 11 close to the surface of the target cell structure 6. In FIG. 1c, a voltage pulse delivered by the voltage generator 2 is applied over the EFC. An electric field is thus established over the cellular structure, causing pore formation due to dielectric breakdown of the cellular membrane. The applied potential also causes electroosmotic or electrophoretic delivery of the solution contained in the EFC. Consequently, the cell-impermeable agent 5 contained in the EFC is delivered at the site of pore formation where the loading agent freely can enter the interior of the cellular target through the generated pores 19. When the electrical field is removed, the formed pores are closed and the cellular membrane heals.

FIG. 2 shows electrolyte-filled capillaries with different tip geometries. As illustrated in FIG. 2a, the EFC 1 may have a perfect cylindrical geometry. It is sometimes advantageous to use capillaries 1 with tapered tip-ends as shown in FIG. 2b and FIG. 2c. This is the case, in particular, for single-cell electroporation. In FIG. 2b, a tapered EFC 1 made by pulling a glass or fused silica capillary in a mechanical puller with a heating filament is illustrated. The tip of such a capillary can be made very small, down to a few nanometers, and the outer diameter as well as the channel diameter is reduced. Tapered capillary can also be prepared created by etching in hydrofluoric acid, or by grinding. The benefit of this approach is that only the outer diameter of the capillary is reduced whereas the inner diameter remains unaffected. This type of capillary is illustrated in FIG. 2c. Capillaries can also be made having conductive tips as illustrated in FIG. 2d and FIG. 2e. The advantage of these hollow capillaries with conductive tips is that shorter pulse times can be applied with high precision because of low RC time constants. The capillary in FIG. 2d has the electrode 3 on the inside, and the capillary shown in FIG. 2e has the electrode 3 on the outside.

DETAILED DESCRIPTION OF THE INVENTION

Figure 3A:
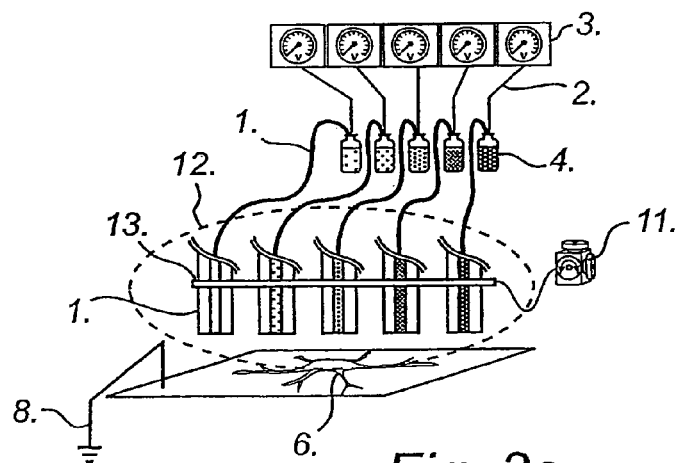
FIG. 3 illustrates delivery of cell-loading agents using multiple EFCs 1 arranged in arrays. Such arrangements of capillaries 1 can be linear arrays 12 as shown in FIG. 3a, or two dimensional arrays 14 as shown in FIG. 3b. These arrays of capillaries can be held together by a holder 13. For electroporation of cell-loading agent delivery to a single cell in rapid sequence, an array of EFCs is swiftly moved over a cellular target, as illustrated in FIG. 3c-e.

As stated above the present invention relates to a highly spatially resolved method for electroporation and parallel delivery, possibly combined with sequential delivery, of single or multiple cell-loading agents to at least one cell structure, such as a cell or cellular structure, in order to transfer said cell-loading agents into said cell structure. More specifically, the disclosed method uses at least two electrolyte-filled capillaries (EFCs) coupled to a voltage or current generator for electroporation of the cell structure wherein the EFCs are placed adjacent to the cell structure and a voltage or current, such as at least one voltage pulse, is applied across the EFCs generating a small electric field outside the terminus of each EFC, which causes pore formation in the membrane of the adjacent cell structure. Single or multiple cell-loading agents contained in the EFCs is/are delivered in a parallel manner at the sites of pore formation, for example by a mode of pumping, allowing the cell-loading agent(s) to translocate the membrane and enter the interior of the cell structure through the pores. In one embodiment, the agents to be loaded into the cells can be selected from a number of containers containing said agents in a combinatorial fashion. The combination of pore formation and delivery of agents supplemented to the electrolyte-solution of the EFCs, enables loading of materials into, for example, the cytoplasm of the cell structure. This is further shown in FIG. 1.

It is stated above that the invention may be used for delivery of membrane-impermeant cell-loading agents to and/or into a cell structure. The cell structure may be either one or several cells or one or several cellular structures. If it is one or several cells, these may be any kind of eukaryotic or prokaryotic cell in confluent culture, tissue slice or tissue. The cell structure may be pre-treated before electroporation. It may, for example, be loaded with a dye such as fluo-3-AM ester for detection of binding events that results in increased concentrations of calcium ion in the cytosol or it may be transfected with a reporter gene or other genetically addressable molecular systems. The cell structures may also be treated by other chemical or physical means, for example in a recording chamber. For example, drugs of interest may be added to the cell bathing solution before during or after the electroporation event. Delivery of such agents can be made through an additional capillary or pipette in connection with the recording chamber either in bulk fashion (to all cells or cell structures or a majority of cells or cell structures) or locally (to a single cell or a single cell structure). It is also possible to use a population of cells, preferably a population of cells or a small population of cells, such as 2 to 10,000,000 cells or 2 to 10,000 cells, in a confluent culture, a tissue slice, a tissue, or an organ, or cells patterned on a surface. Said cellular structure may be an intracellular structure, an organelle (isolated or intracellular), a membranous vesicle, a bacterium or a nanobacterium. It is also possible to use the method according to the present invention on cell structures formed of synthetic membrane structures such as liposomes or emulsion droplets.

With the method according to the invention, it is possible to introduce essentially any kind of substance, agent or cell-loading agent into the electroporated cell structure. With a cell-loading agent is meant an agent that most often is polar and is unable to pass biological membranes spontaneously. Examples of such substances or cell-loading agents include, but are not limited to, the following agents: genes, gene analogs, RNA, RNA analogs, DNA, DNA analogs, colloidal particles, receptors, receptor ligands, receptor antagonists, receptor agonists, receptor blockers, enzymes, enzyme substrates, enzyme inhibitors, enzyme modulators, including allosteric enzyme modulators, proteins, protein analogs, amino acids, amino acid analogs, peptides, peptide analogs, metabolites, metabolite analogs, oligonucleotides, oligonucleotide analogs, antigens, antigen analogs, haptens, hapten analogs, antibodies, antibody analogs, organelles, organelle analogs, cell nuclei, bacteria, viruses, gametes, inorganic ions, organic ions, metal ions, metal clusters, agents that affects cellular chemistry, agents that affects cellular physics, polymers as well as any combination of two or more of these agents.

The electrolyte filled capillaries (EFCs) used are preferably made of an electrically insulating material in order to confine the established electrical field and can be made of glass, fused silica, plastic or polymer, such as Teflon, or any other suitable material. It is also possible to use capillaries with conductive tips. The geometry of the capillaries may be a perfect cylinder with flat ends as shown in FIG. 2a. It is sometimes advantageous to use a tapered capillary as shown in FIG. 2b, in particular, for single-cell and organelle-electroporation. Such tapered capillaries can be made by pulling a glass or fused silica capillary in a mechanical puller with a heating filament (A. Lundqvist, J. Pihl, O. Orwar. A *Anal. Chem.* (2000) 72 5740-5743). Tapered tips can additionally be created by etching in hydrofluoric acid, or by grinding. The benefit of grinding is that only the outer diameter of the capillary is reduced whereas the inner diameter remains unaffected, therefore there is no additional pressure build-up in the tip region in this type of capillary. This type of capillary is illustrated in FIG. 2c.

The length of the capillaries may be from 0.01 mm up to several meters depending on application. Because the voltage drops continuously over the capillary, voltage sources should be chosen accordingly to ascertain that large enough voltages may be applied to cause pore-formation in the targeted cell or cellular structure. The outer diameter and channel dimension of the capillary depends on application. In general terms, the diameter of the end of the EFC closest to the cell structure is from a few nanometers to several thousand micrometers, such as from 50 nm to 5,000 μm. For single cell and organelle electroporation it is often suitable to use capillaries with an outer diameter of 0.03-50 μm and a channel diameter of 0.025-49 μm whereas for electroporation of small populations of cells capillaries larger than 50 μm are preferably used.

When using electrically insulating capillaries, the electrical current needed for electroporation of a cell structure is carried by the electrolytes contained in the solution in the inner channels of the capillaries. The electrodes, preferably Pt-electrodes, that feeds current supplied by a voltage generator into the capillary system, can be connected directly to the back-end of the electrolyte-filled capillary or via a vial containing the same electrolyte solution as inside the EFC. Because the vial containing the electrode and the capillary inlet is, typically, several centimeters away from the capillary outlet there will be no problems with electro-generated species that potentially can harm the cells. Sometimes it is preferable that the vial also contains the agents to be internalized into the cell structure. It is also possible to place the electrode inside the electrolyte-filled capillary. This is preferable when using capillaries of very short length. Depending on the composition of the buffer the conditions are changed at the electrodes. Electrochemical reactions at the electrodes, e.g. reduction of water and oxidation of chloride, cause some loss in voltage and the effective voltage should be calculated for every given set of electrode materials and buffer systems.

Capillaries can also be made with layers of conductive materials at their tip as shown in FIG. 2d-e. The advantage of such hollow capillaries with conductive tips is that shorter pulse-times can be applied with high precision because of low RC time constants.

It is stated above that the fluid containing the cell-loading agents is delivered to the cell structure by some mode of pumping. This mode of pumping may, for example, be electroosmosis, electrophoresis, pressure based pumping or gravitational flow or combinations thereof. Preferably electrophoretic or electroosmotic transport of fluid is used for reagent delivery. It is important to note that these modes of pumping require that the inner surface area of the capillary be electrically charged. When electroosmosis or electrophoresis is not used for pumping, any appropriate apparatus for creating the flow such as a peristaltic pump, a microinjector/micropump or other devices for driving fluids needs to be connected to the inlet of the EFC either before, during, or after electroporation. It may sometimes be advantageous to deliver agents to cells using a pumping method and apply electric pulses for electroporation periodically. For example, a volume of electrolyte contained in an EFC is pumped using a peristaltic pump to the cell surface and the electroporation voltage is turned on whereafter the electroporation voltage is turned off, and a new volume of electrolyte is pumped to the cell surface through the same EFC and the electroporation voltage is again turned on whereafter the electroporation voltage is turned off and so on. This type of delivery with periodic electroporation may, in particular, be advantageous when segmented bands (discrete zones) of different cell-loading agents are present in the EFC. Such bands may be obtained using the microfluidic switching method described below. In addition to the example above many different schemes can be envisioned in which the voltage generator is programmed or manually controlled to provide for optimal loading conditions for different types of cell-loading agents and cells. Thus, both pulse duration, waveform, pulse amplitude, and other pertinent parameters may be changed during the course of cell-loading using an EFC. Thus, it is preferable that according to the present invention, a programmable voltage generator is used.

One or several EFCs for electroporation can be used together with a single counter, or second, electrode of different size and material. The electrodes can be placed adjacent to a cell for electroporation of the cell membrane. Preferably, a counter electrode that keeps the cell-bathing solution at ground potential is used.

The EFC is, as the term implies, filled with an electrolyte-containing solution. Preferably physiological buffers are used. The cell-loading agents to be introduced into the cytosol of the cellular target is preferably supplemented to this electrolyte containing solution. In addition, the EFC may be supplemented with drugs, or agents, interacting with targets located in the cell plasma membrane. Such targets includes plasma-membrane-bound receptors and enzymes. Injection, or filling, of an EFC can be achieved in several different ways using standard techniques for filling CE capillaries. For example, the electrolyte solution is injected into the capillary hydrodynamically, using gravity flow or by using some mode of pressure based pumping.

It is sometimes preferable to load the capillaries from the tip end using capillary forces or aspiration/suction. This procedure can be used to load a plurality of EFCs simultaneously. The tips of the EFCs are positioned in individual vials containing cell-loading agents and a small sample is introduced into the EFCs using any of the above mentioned methods.

The voltage pulse for creating pores in cell membranes delivered by a voltage generator, may have a waveform that can be square, exponential, or of any other form. It is also possible to use both DC currents and AC currents. Because the voltage drops continuously over the capillary, voltage sources should be chosen accordingly to ascertain that large enough voltages may be applied to cause pore-formation in the targeted cell or cellular structure. The electrical fields needed to cause electroporation vary largely depending on the type and the size of the treated cell structure. As stated above, it is also possible to vary the potential and waveform over the EFC during the time course of agent delivery to a cell structure, i.e. delivery and electroporation is not performed at a constant electric potential or electric field strength. Such voltage programming is preferably used when several compounds are introduced to a cell structure in a sequential manner. The duration of the voltage pulse may vary from a few microseconds to several minutes, depending on the type and the size of the treated cell structure as well as depending on the nature of the cell-loading agent.

During application of the voltage or current pulse, the cell structure is permeabilized through pore formation, allowing polar solutes that otherwise cannot pass through the biological bilayer membranes, to enter the interior of the cell structure through diffusion or hydrodynamic flow. The spatial resolution of the method according to the invention is dictated by the tip-size of the EFC, which can be made to be only a few nanometers in diameter, the applied voltage and the gap distance between the EFC and the electroporation target. This gap distance depends mainly on what type of cellular structure is to be electroporated and may thus vary between a few nanometers to a few hundred micrometers.

Positioning of the EFC is preferably achieved by the action of manually controlled micropositioners such as hydraulically or piezoelectrically controlled micromanipulators. In addition to using manually controlled micropositioners it is feasible to use automatically controlled or robotically controlled micropositioners. Rather than moving the capillary while keeping the cell fixed, it is also possible to use motorized translation stages mounted on microscopes or other similar devices for moving the cell while keeping the capillary fixed.

When using the method according to the invention for intracellular screening applications, preferably a large number of different cell-loading agents are introduced to the cytosol of one or several cells, or cellular structures, in a controlled fashion. Screening is preferably achieved using parallel delivery, possibly combined with sequential delivery, of loading agents to the cellular target and may, for example, be accomplished as described below.

Parallel delivery of multiple cell-loading agents may be achieved using EFC arrays. Arrays of EFCs may be fabricated using microfabrication techniques, thus comprising one solid structure, or be composed of several conventional EFCs held together by some type of holder or scaffold. These arrangements of capillaries can be one-dimensional arrays (linear), or two-dimensional arrays. Preferably arrays of 10-100,000 EFCs are used.

Parallel electroporation and delivery enables simultaneous screening of several physically separated single-cells, or populations of physically separated cells, in a parallel fashion.

Figure 6:
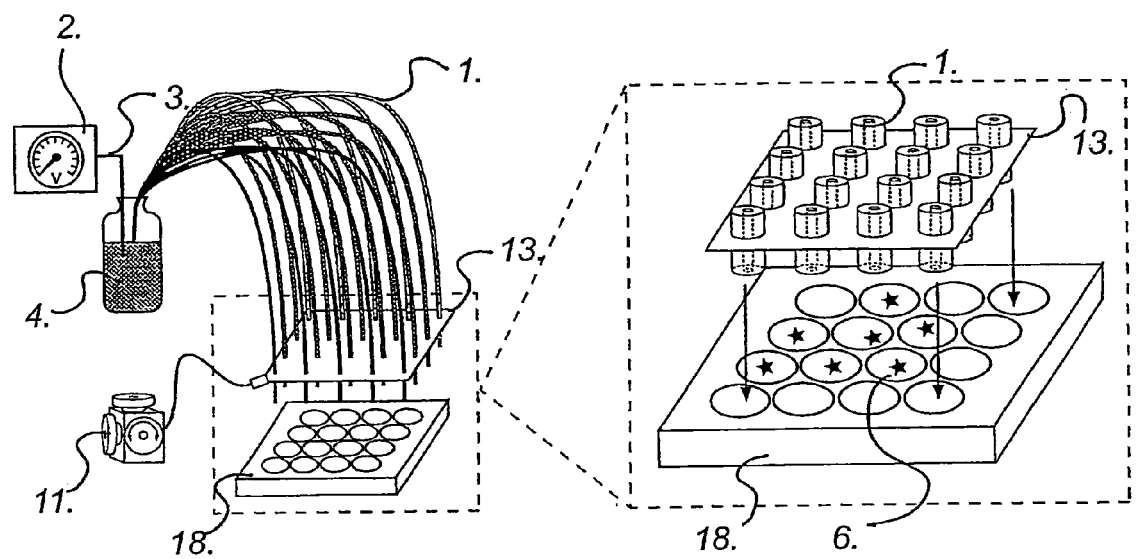
FIG. 6 illustrates one example of parallel electroporation of cells grown in patterns on a surface or cells contained in multiple wells in a multi-well plate. Cells grown in patterns on a surface or cells contained in multiple wells in a multi-well plate are ideally suited for the two dimensional (2-D) EFC array format here illustrated. In each case a single capillary outlet targets a specific cell 6 or a population of cells 6 on a surface or, as illustrated here, in a well structure 18.

According to one embodiment the cell structure consists of cells grown in patterns on a surface or cells contained in multiple wells in a multi-well plate, as illustrated in FIG. 6. The plate may, for example, be a standardized industrial plate having, for example 96 wells. In parallel cytosolic delivery of cell-loading agent each single capillary outlet in an array of capillaries targets a specific cell or a population of cells on a surface or in a well structure. Thus, individual cells or populations of cells can be individually targeted with the same, or different, compounds that are internalized into the cytoplasm simultaneously.

Figure 7A:
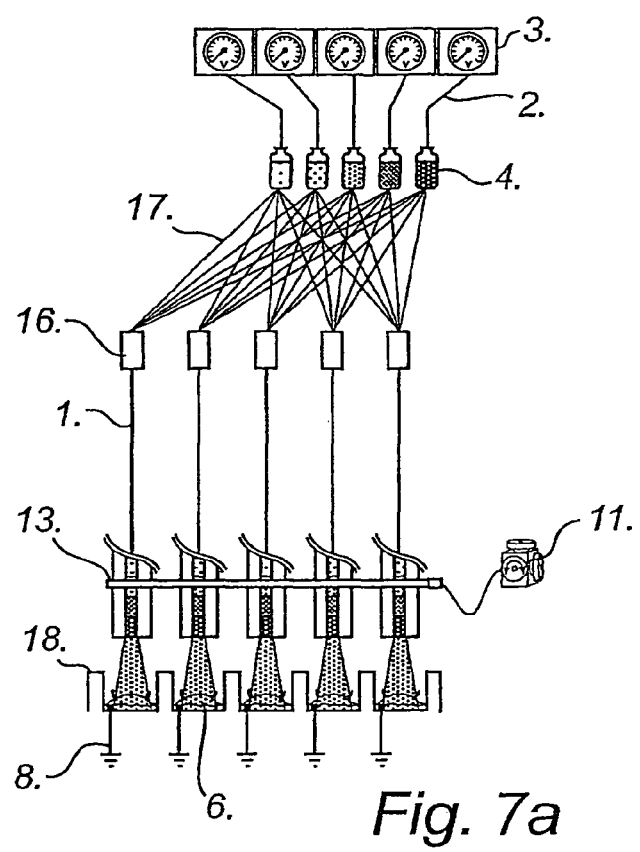
In FIG. 7a, several individual cells, located in separate wells in a multi-well structure 18, are subjected to simultaneous (parallel) electroporation after sequential delivery of cell-loading agents. This setup also allows combinatorial delivery of cell-loading agents as illustrated in FIG. 7b where each EFC in the array is loaded with different sequences of cell-loading agents.
Figure 7B:
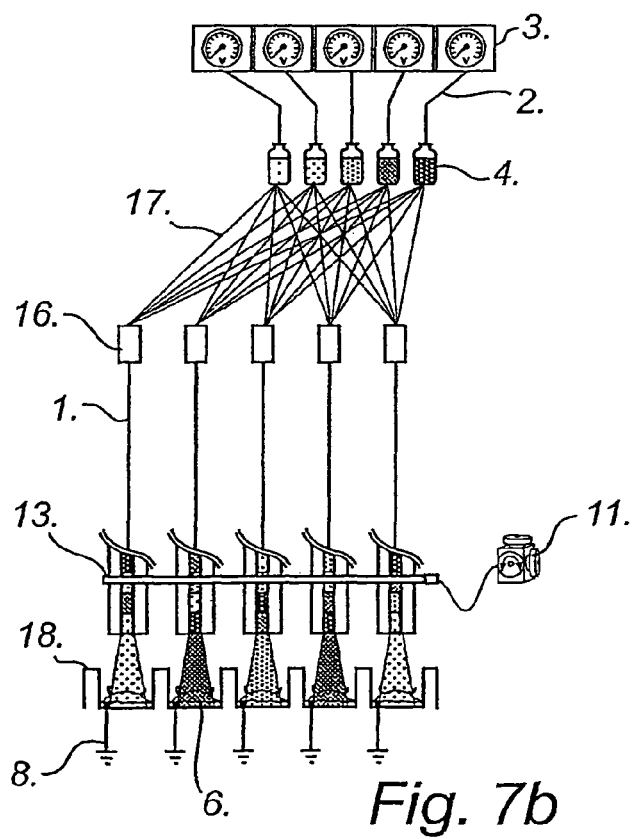
FIG. 7 shows one embodiment for parallel delivery of cell-loading agents with the present invention. Each EFC 1 in an array is here connected to a microfluidic switch 16 enabling loading of multiple cell-loading agents into the EFC in sequence to obtain discrete zones of said cell-loading agents in said EFC. Because several different cell-loading agents contained in separate vials can be selected, each EFC in the array can be loaded with any given sequence/combination of cell-loading agents.

A preferred embodiment for parallel screening with the present invention is illustrated in FIG. 7.

Figure 3B:
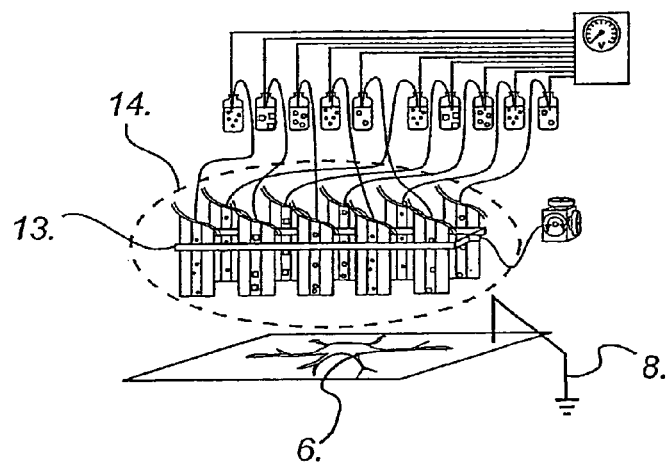
Figure 3C:
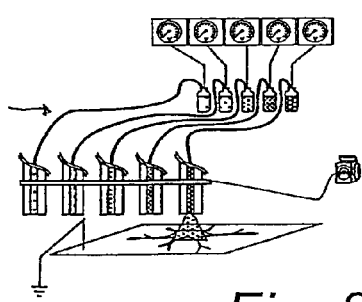
Figure 3D:
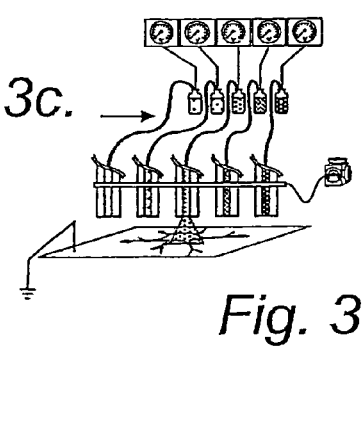
Figure 3E:
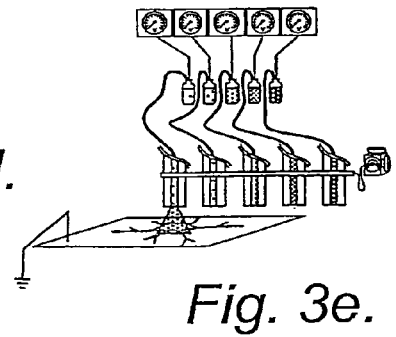

The parallel delivery of cell-loading agents can be performed together with sequential delivery of cell-loading agents in a combinatorial fashion. Such combinatorial delivery may be achieved by selection of cell-loading agents to each EFC from a plurality of containers containing said cell-loading agents as shown in FIG. 3b. It may also be achieved by activating different EFCs in an array of EFCs where each EFC contains different cell-loading agents. It may also be achieved by loading of agents in specific order into a single EFC using a microfluidic switching devices as shown in FIG. 7.

There are several embodiments of sequential delivery suitable for use together with the parallel delivery according to the invention. Below are some examples of suitable embodiments given.

Figure 4:
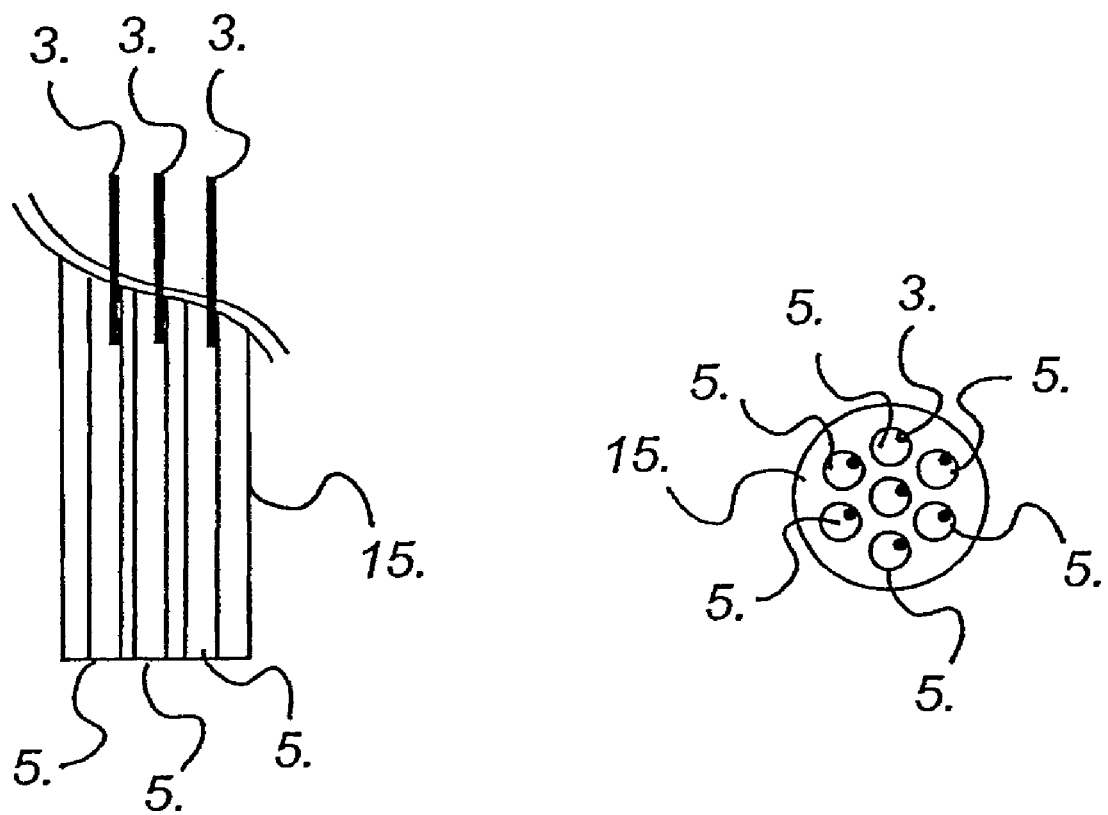
FIG. 4 shows a special type of EFC array, namely an EFC of multiple barrel-type 15 wherein the EFC comprises several barrels 5 or channels 5, each equipped with an individually addressable electrode 3 and filled with a single, or several, cell-loading agents 5 as illustrated in FIG. 3a (side view is illustrated at left side and front view at the right side). By sequential voltage application in individual barrels it is possible to sequentially deliver controlled amounts of loading agents using this arrangement.
Figure 5A:
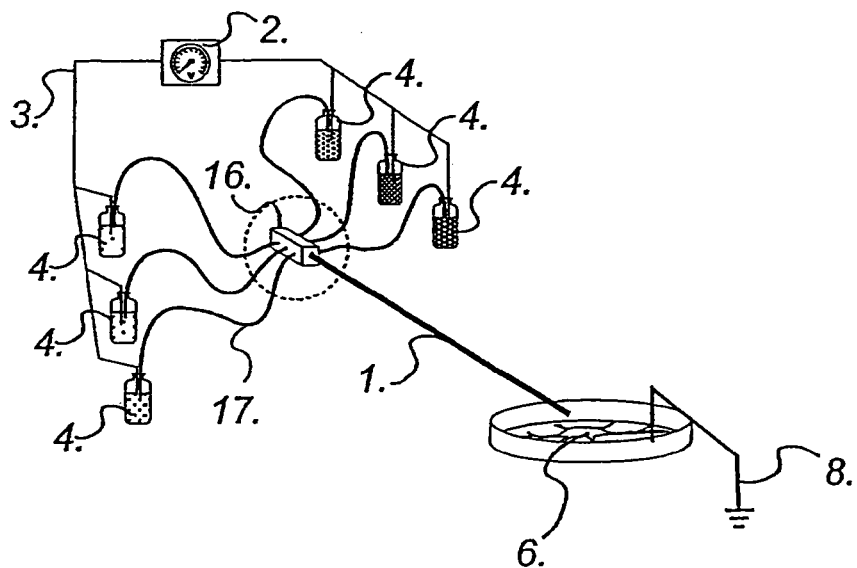
FIG. 5 illustrates cell-loading agent delivery accomplished by using microfluidic switches for sequential loading of an EFC to obtain discrete zones of cell-loading agents in said EFC. This concept is illustrated in FIG. 5a, where one EFC 1 is connected via a microfluidic switch 16 and feeder EFCs 17 to six different vials 4 containing different loading agents. The vials are equipped with individually addressable electrodes 3. By sequential application of a voltage pulse to each vial 4, cell-loading agents are pumped via the feeder EFCs into the microfluidic switch where they enter the main EFC 1 in a sequential manner. Discrete bands of cell-loading agents are thus formed in the main EFC that can be introduced for the electroporation target 6. This loading procedure is illustrated in FIG. 5b-d.
Figure 5B:
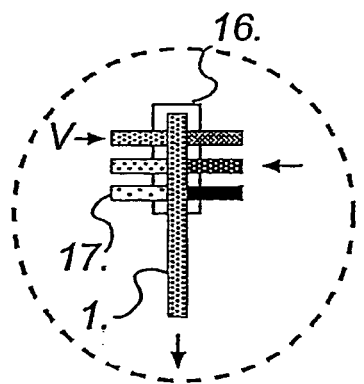
Figure 5C:
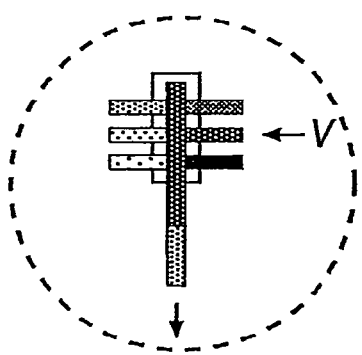
Figure 5D:
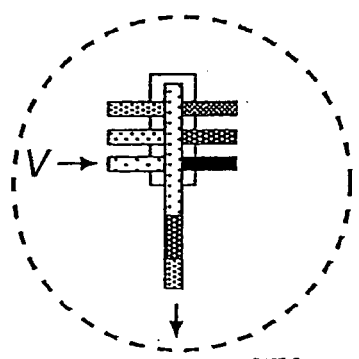

According to one embodiment, sequential delivery of multiple cell-loading agents is achieved using EFC arrays. Arrays of EFCs may be fabricated using microfabrication techniques, thus comprising one solid structure, or be composed of several conventional EFCs held together by some type of holder or scaffold. These arrangements of capillaries can be one-dimensional arrays (linear), or two-dimensional arrays. Preferably arrays of 10-100,000 EFCs are used. To achieve sequential delivery of loading agents in this embodiment of using EFC arrays, each EFC contains one type of loading agent or a unique mixture of several loading agents. Sequential delivery can be achieved by swiftly moving the array of EFCs over a cellular target in rapid sequence, each EFC is causing electroporation and subsequent delivery of one type of loading agent or unique mixture of several loading agents. Instead of moving the array of capillaries, it is also possible to move the cell structures in relation to spatially fixed capillaries. Fluidic pumping in these arrays can be generated by any of the pumping modes discussed above. Examples of one- and two-dimensional arrays that according to this embodiment may be used for sequential cell-loading agent delivery are illustrated in FIG. 3. A special type of array is the multiple barrel-type EFC illustrated in FIG. 4. This capillary is characterized by having several inner channels. To achieve cytosolic delivery of cell-loading agents or unique mixture of several loading agents, each barrel in the capillary is filled with a single type of loading-agent or unique mixture of several loading agents and equipped with an individually addressable electrode. By sequential activation of individual barrels, i.e. by consecutive application of voltage pulses in single channels, it is possible to sequentially deliver controlled amounts of loading agents to cells or cellular structures. This type of multi-barrel electrode can also be used for parallel delivery of agents to a cell structure by simultaneously applying voltage to more than one channel. Fluidic pumping in multiple barrel EFCs is preferably achieved by using electroosmotically or electrophoretically generated flow. The number of different agents that can be delivered with this approach is, however, limited by the number of barrels in the EFC. It is also possible to create arrays of multiple barrel-type EFCs as discussed above.

According to another embodiment, sequential delivery of multiple cell-loading agents is achieved by connecting a conventional EFC to a microfluidic switch for sample stacking. In this configuration a plurality of loading agents can be sequentially introduced into the EFC and subsequently be delivered to a single or several cellular targets. The cell-loading agents can be introduced in discrete zones in the EFC by any of the pumping modes discussed above. Either the EFC is preloaded with cell-loading agents before electroporation experiments or the EFC is loaded on-the fly, that is during electroporation experiments. An example of this second embodiment is illustrated in FIG. 5.

According to yet another embodiment, sequential delivery of multiple cell-loading agents is achieved by introducing a separation step while pumping the fluid through the EFC. When using electrophoretic pumping for delivery of reagents, all species present in the electrolyte solution is separated based on their charge-to-frictional drag ratio and will be delivered in a sequential manner at the cellular target. Analogously, sequential reagent delivery can be achieved by incorporating any separation technique applicable to the EFC format, for example, it is feasible to utilize chromatographic separation techniques.

Thus, the present invention may be used in rapid intracellular screening applications comprising any of the following modes:

1. Intracellular delivery of membrane-impermeant cell-loading agents to a single cell or population of cells of one cell type.
2. Intracellular delivery of membrane-impermeant cell-loading agents to physically separated single cells or population of cells of the same cell-type.
3. Intracellular delivery of membrane-impermeant cell-loading agents to physically separated single cells or population of cells of different cell-types.
4. Sequential intracellular delivery of membrane-impermeant cell-loading agents to a single cell or population of cells of one cell type
5. Sequential intracellular delivery of membrane-impermeant cell-loading agents to physically separated single cells or population of cells of the same cell-type.
6. Sequential intracellular delivery of membrane-impermeant cell-loading agents to physically separated single cells or population of cells of different cell-types
7. Parallel intracellular delivery of membrane-impermeant cell-loading agents to a single cell or population of cells of one cell type.
8. Parallel intracellular delivery of membrane-impermeant cell-loading agents to physically separated single cells or population of cells of the same cell-type.
9. Parallel intracellular delivery of membrane-impermeant cell-loading agents to physically separated single cells or population of cells of different cell-types.
10. A combination of parallel and sequential intracellular delivery of membrane-impermeant cell-loading agents to a single cell or population of cells of one cell type.
11. A combination of parallel and sequential intracellular delivery of membrane-impermeant cell-loading agents to physically separated single cells or population of cells of the same cell-type.
12. A combination of parallel and sequential intracellular delivery of membrane-impermeant cell-loading agents to physically separated single cells or population of cells of different cell-types.
13. Any mode of intracellular delivery of cell-loading agents described above (1-12) that is used in a combinatorial fashion.

The most important applications of the method according to the present invention, is for use in drug screening and protein identification. In particular, by applying a permeabilizing electric field over cells or cellular structures, specific probes (markers), substrates or ligands can be introduced into the cytoplasm to screen for intracellular chemistry such as cytosolic enzymes and receptors on organelles. More specifically, this would allow screening of intracellular drug action as well as assaying of intracellular proteins such as enzymes, receptors or structural proteins. Using the method according to the pre-sent invention, these markers can be introduced in combination with drugs or ligands that interact directly with the target protein or proteins in the same signaling pathways. Thus, according to the present invention it is possible to characterize, even on the single cell level, both the presence of various proteins and their function. Blocking of particular pathways with specific ligands, antagonists, inhibitors or modulators might enable control of cellular processes and provide leads for novel systems. Such compounds can be introduced to a cell either by co-electroporating them using an EFC with the ligand of interest. Alternatively, they may be internalized in a cell structure by other means, for example, cell-permeable agents may be employed.

In general terms, the method according to the invention can be used in the following, non-limiting, areas of applications: proteomics, genomics, phenotype profiling, drug assays and screening, pharmacokinetics, in vitro fertilization, transgenics, nuclear transfer, organelle transfer, and diagnostics. Also, because the technology can be used to change properties of cells, i.e., cellprogramming and that this programming can be performed in networks of cells the invention is also useful in design and application of biological and chemical computers as well as biosensors. Likewise the invention can be useful in robotics, in particular, to create cell circuits with specific properties such as cellular sensory networks and cellular control networks.

The method according to the invention may also be combined with screening techniques for surface plasma membrane epitopes or receptors. Thus, for example, a receptor ligand acting on a cell plasma membrane receptor may be combined in the EFC electrolyte with one or several drugs acting on intracellular chemistry. The solution can then be delivered to the cell surface at low non-permeabilizing or zero electric fields, and after the ligand acting on a cell plasma membrane receptor has bound to the receptor, the internalizing agents are introduced into the cell with electroporation. Such methods might in particular be suitable for characterization of signaling pathways.

More specific, but still non-limiting, applications in which the method according to the invention can be used are gene transfection, gene identification, enzyme identification, protein identification, receptor identification, binding assays, enzyme assays, competitive enzyme assays, non-competitive enzyme assays, enzyme assays with modulators, enzyme assays with isosteric inhibitors, receptor assays, receptor assays with antagonists, receptor assays with modulators, viral assays, bacterial assays, drug assays, kinetic assays, modification of metabolic pathways, and modification of signaling pathways.

Specifically, the method according to the invention is very suitable for identification of intracellular receptor and receptor ligands.

Figure 8:
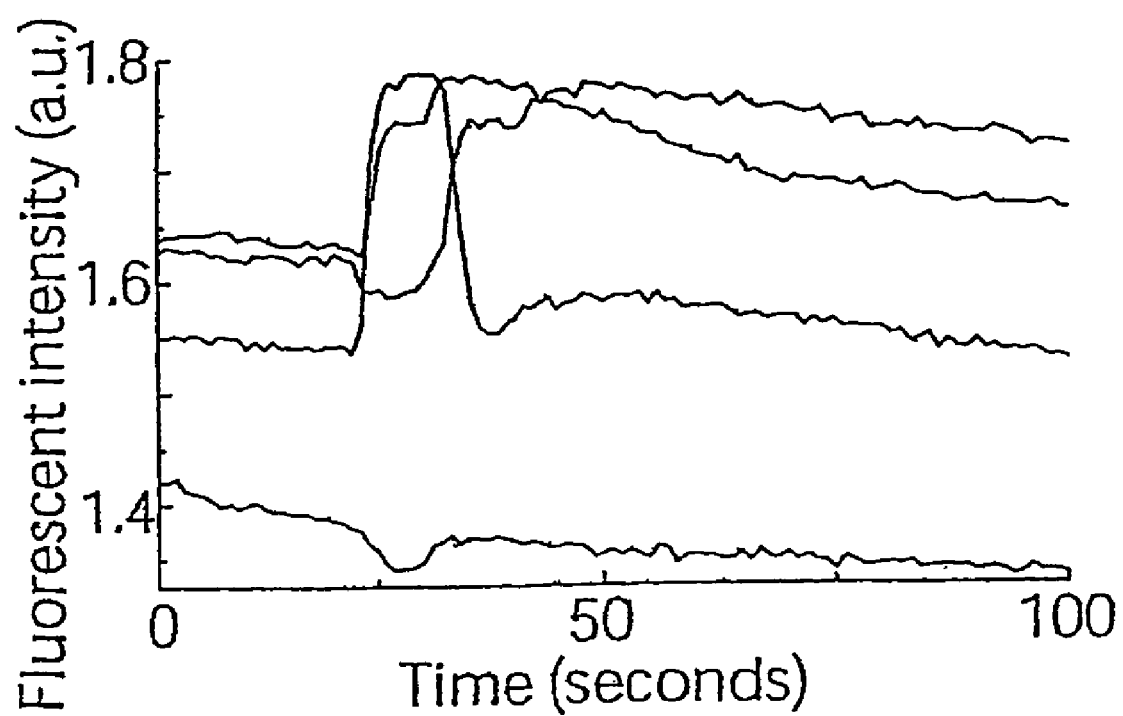
FIG. 8 is a plot of fluorescence versus time from identification of intracellular rhyanodine type II receptors in fluo-3-stained NG108-15 cells.

Intracellular receptors and ion channels that cause release of signaling molecules such as $Ca^{2+}$, cAMP, $K^+$ etc. can be identified and studied using ligand libraries that are electroporated into cells, preferably in combination with selective receptor antagonists. For example, $Ca^{2+}$ released from intracellular stores upon activation of an intracellular receptor can be detected using fluorogenic chelating agents such as magfara-2 and fluo-3. As an example we here show identification of ryanodine receptors of the endoplasmic reticulum (FIG. 8). Furthermore, to identify the receptor, or to reveal receptor-ligand interactions, a selective receptor antagonist may be used and electroporated into the cell to selectively block the action of the ligand. In addition to fluorescence probes, radio ligands, blotting or electrophysiological methods, and fluorogenic substrates can be used. Fluorogenic markers are often cellpermeant esters that can be added to the cell bath medium and need not be electroporated into cells. Thus using such esters, cells can be loaded with dyes before electroporation experiments. By having the ability to introduce both a receptor agonist in addition to a marker for the specific receptor activation it is possible to identify the most potent receptor agonist from a library of agonists. It is also possible to design experiments to obtain dose-response curves. For example, with the method according to the present invention it is possible to introduce both a receptor agonist and a receptor antagonist into the cell cytosol at different concentrations of the respective compound in addition to a marker for the specific receptor activation. It is also possible to introduce both a receptor agonist and a receptor antagonist into the cell cytosol at different concentrations of the respective compound with the overall aim to find out the nature of the receptor agonist and the receptor antagonist binding, i.e. whether it is competitive or non-competitive, etc. In addition to identification of receptors, and ligands also the so-called "ligand fishing" or "de-orphaning" can be performed in this way. A cell with a known set of receptors is used as detectors and a library of potential sample of ligands are introduced to the cell cytosol to screen for the actions of these ligands.

Furthermore, the invention is suitable for identification of intracellular enzymes and enzyme substrates.

Highly specific enzymes substrates that results in fluorescent products can be used for protein/enzyme identification in, for example, proteomics and phenotype profiling of individual intracellular systems using the technique according to the invention. The synthetic substrate, possibly in combination with a drug, inhibitor, or modulator, can be introduced into the cell using electroporation according to the present invention. There are a variety of substrates available that can be employed as light switches in the substrate-product conversion step. Such substrates includes substrates for esterases, sulfatases, phosphatases, and so on. Either substrate is fluorescent and the product is non-fluorescent or vices versa.

For coupled reaction systems within cells—, for example, the degradation of alcohol by the alcohol dehydrogenase that utilize the conversation of $NAD^+$ to—$NADH$, thus causing a shift in fluorescence—the target molecule need not be fluorescent as long as it is coupled to a reaction that yields a detectable molecule. Other examples of such native fluorescent compounds in cells are NADPH and Ravines.

Chemical amplification with enzymes can also be used to increase the sensitivity of the system (W. J. Blaedel, R. C. Bougslaski, Anal Chem 1978, 50, 1026; H. U Bergmeyer in H. U. Bergmeyer (ed) methods of Enzymatic Analysis, verlag Chemie/Academic Press, New York 1974 vol 1 p 131). The principle of this method is to use enzymes that turn the substrate into products, and thus cause a large concentration change from substrate, which may be difficult to measure, into products, which can be readily measured.

One example of a fluorogenic substrate is fluorescein diphosphate (FDP) that can be used for detection of phosphatases. The substrate is hydrolyzed by alkaline phosphatase and yield the fluorescent product fluorescein. Another system is the casein-BODIPY FL, which is substrate for metallo-, serine, acid and sulfhydryl proteases, including cathepsin, chymotrypsin, elastase, papain, pepsin, thermolysin and trypsin. Other examples of systems are β-galactosidase where the substrate is fluorescein di-β-D-galactopyranoside (FDGP) which sequentially hydrolyzed by β-galactosidase, first to fluorescein monogalactoside (FMG) and then to highly fluorescent fluorescein.

Figure 9:
FIG. 9 shows the results of detection of intracellular proteases using casein-BODIPY-FL.
Figure 9:
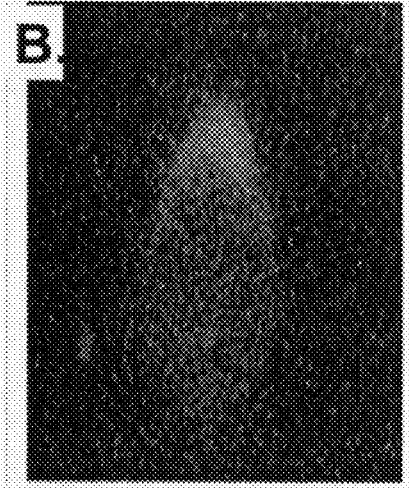
Figure 9:

FIG. 9 shows the experimental result of using Fluorescein diphosphate (FDP) to target the intracellular enzyme alkaline phosphatase that catalytically hydrolyses the phosphoesterbonds on the substrate so that the highly green-fluorescent product fluorescein is formed in the cytosol (FIGS. 9A-C). The substrate fluorescein diphosphate (FDP) was supplemented to the electrolyte of the EFC into the cell. The substrate is non-fluorescent and the product is fluorescent. The fluorescence obtained in the cell in FIG. 9B, which indicates the presence of the product, signals also the presence of the enzyme.

Protein-protein interactions are complex and involve many processes. Blocking of particular pathways with specific ligands might enable control of cellular processes and provide leads for novel systems (Zutshi R, Brickner M, Chmielewski J, Inhibiting the assembly of protein-protein interfaces, Curr. Opin. Chem. Biol. 1998 2 62-66). For example, the intracellular protease activity was investigated using a protein, casein, which was heavily loaded with the green-fluorescent molecule BODIPY FL, as enzyme substrate. In solution, casein-BODIPY FL is folded so that the quaternary arrangements in the molecule quench the fluorescence. When the peptide bonds are cleaved, by the action of cytosolic proteases, segments of free peptides tagged with BODIPY FL starts to fluoresce. Images in FIG. 10A-C, show the identification of proteases in a single NG108-15 cell.

The invention will be further illustrated in the examples below, which in no way limit the scope of the invention.

EXAMPLE 1

Detection of the Intracellular Receptor Ryanodine Type II

Fluo-3 AM ester was from Molecular Probes (Leiden, The Netherlands). Cyclic ADP ribose and the chemicals used for buffer solutions, were all of analytical grade and purchased from Sigma (St. Louis, Mo., USA). All solutions were made in distilled water from a Milli-Q system (Millipore).

NG108-15 cells were plated on no. 1 cover slips or in a Petri dish and allowed to grow for 1-3 days. Cell dishes were mounted in a circular polycarbonate holder and transferred to the stage on the microscope. Prior to experiments the culture medium was replaced by a HEPES buffer (NaCl 140 mM, KCl 5.0 mM, $MgCl_2$ 1.0 mM, $CaCl_2$ 1.0 mM, D-glucose 10 mM, HEPES 10 mM, pH was adjusted to 7.4 with NaOH).

The cells were stained with fluo-3 AM ester by incubating the cells for 30 minutes in dye solution (10 µM fluo-3 AM ester in HEPES buffer) at room temperature. To remove excess uncaptured dye, the cells were washed three times in HEPES buffer and stored for an additional 30 minutes in HEPES buffer before the experiment.

Excitation of fluorophores was performed with an $Ar^+$- laser (SpectraPhysics 2025-05, Sunnyvale, Calif.). The laser beam was sent through a spinning disk to break the coherence, a 488 nm line interference filter (Leica I-3 filter cube), and focused onto the cover slips using a 40× objective (Leica 0.9 N.A.) mounted in an inverted microscope (Leica DMIRB, Wetzlar, Germany). Images were recorded with a 3-chip color CCD-camera (Hamamatsu C6157, Kista, Sweden).

Electroporation was performed with an electrolyte-filled capillary (30 cm long, 50 µm id., 375 µm o.d.) positioned 20-35 µm above the cell with a high-graduation microman- ipulator (Narishige, MWH-3, Tokyo, Japan). To position the EFC at a specific distance, the cell was first brought in focus by observing the cell in the microscope. Then the focus was changed using the micrometer markers on the focusing knob of the microscope to the desired distance above the cell. The EFC was lowered until the lumen of the EFC came in focus. After the right position was set, the focus was returned to the cell. The cell-bathing medium was grounded with a platinum wire. A pulse was applied with a DC high voltage power supply (model ARB 30, Bertan, Hicksville, N.Y., USA) for a duration of 5-20 seconds.

The agonist cyclic ADP ribose was used to detect the ryanodine receptor type II in NG108-15 cells. Cyclic ADPR (500 µM) was added to the electrolyte of the EFC. When the high voltage pulse was applied, pores were formed in the cell plasma membrane while the introduction of the agonist into the cell was improved by the electroosmotic administration of the agonist toward the cell surface. When the agonist binds to the ryanodine receptor on ER, calcium is released into the cytosol. The ryanodine receptor type II was detected by adding cADPR (500 µM) to the electrolyte of a 50 µm id., 30 cm long EFC. 10 kV was applied for 10 seconds. Upon activation, the ryanodine receptor triggers a release of calcium ions from ER, which bind to fluo-3 and the increase in fluorescence, was measured (FIG. 8). Different cells responded slightly differently to the stimulation and therefore three response curves (upper traces) are shown. The response-rate was 60% (n=17). The voltage pulse was applied after 20 seconds. The lower trace is a blank runs where intracellular buffer was introduced using the EFC. A small decrease in fluorescence can be observed due to leakage of dye through the formed pores. Using dyes, such as fura-2, which enters the ER, such effects are largely avoided.

EXAMPLE 2

Detection of Intracellular Enzymes I, Detection of Proteases

Casein BODIPY FL was obtained from Molecular Probes (Leiden, The Netherlands). The chemicals used for buffer solutions were all of analytical grade and purchased from Sigma (St. Louis, Mo., USA). All solutions were made in distilled water from a Milli-Q system (Millipore).

Cell culturing and preparations were made according to methods used in example 1 above, and apparatus and instrumentation was the same as in example 1.

Electroporation was performed as in example 1 and an EFC (30 cm long, 50 µm id., 375 µm o.d.) was used. Casein BODIPY FL was used in a concentration of 100 µg/ml and electroporated into cells using a 10 second pulse at 10 kV.

The results of detection of intracellular proteases using casein-BODIPY-FL is shown in FIG. 9. Specifically, the intracellular protease activity was investigated using a protein, casein, which was heavily loaded with the green-fluorescent molecule BODIPY FL, as enzyme substrate. In solution, casein-BODIPY FL is folded so that the quaternary arrangements in the molecule quench the fluorescence. When the peptide bonds are cleaved, by the action of cytosolic proteases, segments of free peptides tagged with BODIPY FL starts to fluoresce. Images in FIG. 9A-C, shows the identification of proteases in a single NG108-15 cell.

Casein BODIPY FL was introduced and fluorescence intensity was monitored 30 second after electroporation. The response-rate was 60%, n=19. The enzyme activity can be correlated to the increase in fluorescence, which means that this method is suitable for screening and determination of enzyme activity in single cells. This can be useful for single cell proteomics where differences in enzymatic activity would reveal phenotypes in a cell population.

EXAMPLE 3

Detection of the Intracellular Enzyme Alkaline Phosphatase

Fluorescein diphosphate was obtained from Molecular Probes (Leiden, The Netherlands). The chemicals used for buffer solutions were all of analytical grade and purchased from Sigma (St. Louis, Mo., USA). All solutions were made in distilled water from a Milli-Q system (Millipore).

Methods and procedures for cell culturing and preparation were the same as used in example 1.

Electroporation was performed according to example 1. FDP was supplemented to the electrolyte at a concentration of 500 µM. Parts of the substrate fluorescein diphosphate were already present as fluorescein. Therefore the cell was bleached during the electroporation event (pulse length 5 seconds, 10 kV) plus 10 extra seconds after the pulse to eliminate excess fluorescein from the cells. Cells were viewed 30 seconds after the electroporation and thereafter in 30-second intervals. The EFC (30 cm long, 50 µm id., 375 µm o.d.) was moved from the cell before viewing.

The apparatus and instrumentation was the same as used in example 1.

Figure 10:
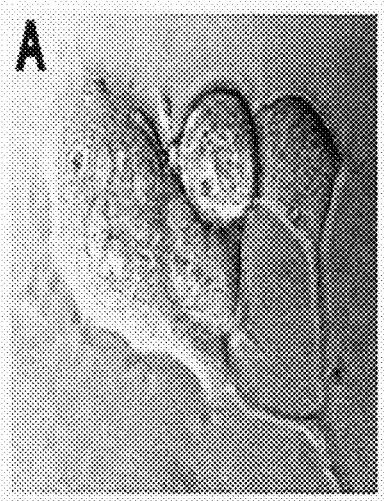
FIG. 10 shows the results of identification of alkaline phosphatase in NG108-15 cells.
Figure 10:
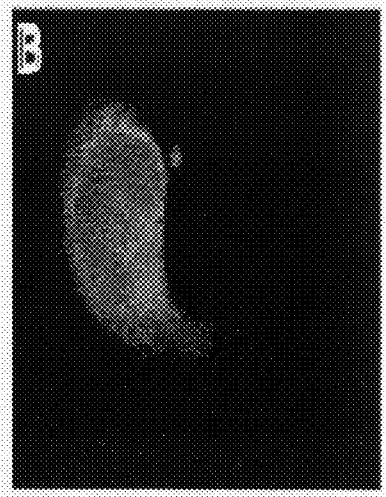
Figure 10:
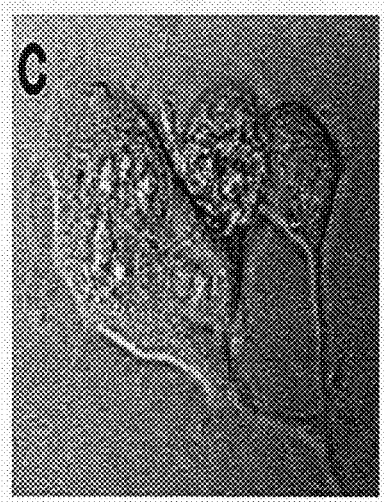

The results of the identification of alkaline phosphate in untreated NG108-15 cells is shown in FIG. 10. Fluorescein-diphosphate (FDP) was used to target the intracellular enzyme alkaline phosphatase that catalytically hydrolyses the phosphoester-bonds on the substrate so that that the highly green-fluorescent product fluorescein is formed in the cytosol, FIG. 10A-C.) A cell was chosen and the substrate fluorescein diphosphate (FDP) was supplemented to the electrolyte of the EFC. In FIG. 10A a high voltage pulse (5 seconds, 10 kV) was applied. 30 seconds after the electroporation event the fluorescence was measured with a charged coupled device (CCD) camera. The substrate is non-fluorescent and the product fluorescent. The fluorescence obtained in the cell in FIG. 10B is therefore a proof of presence of the enzyme.

The response rate was 70% (n=8). FIG. 10C shows the same cell after the electroporation event.

The invention claimed is:

1. A method for parallel delivery of two or more agents to a surface of one or more cell structures and into the cytoplasm of the one or more cell structures comprising:
   (a) providing at least two electrolyte-filled tubes together with a ground or counter electrode,
   (b) connecting the electrolyte-filled tubes to a voltage or current generator,
   (c) introducing at least two agents into the electrolyte solution contained in each electrolyte-filled tube, wherein each electrolyte-filled tube used comprises at least two agents, which are arranged in at least two discrete zones or bands whereby the at least two agents are sequentially delivered through the pores of the one or more cell structures,
   (d) placing the electrolyte-filled tubes at close distance to the surface of the one or more cell structures,
   (e) sequentially transporting the agents through the electrolyte-filled tubes to the surface of the one or more cell structures, and
   (f) focusing an electric field of a strength sufficient to obtain electroporation of the surface of the one or more cell structures on the one or more cell structures, resulting in formation of pores in the membrane surface of the one or more cell structures, and
   wherein the agents are sequentially transported through the pores formed in step (f) and into the cytoplasm of the one or more cell structures,
   wherein steps (a-f) are performed in consecutive order, with the exception that the order of steps (b), (c) and (d) may be altered, and that the order of steps (e) and (f) may be altered.

2. A method according to claim 1, wherein agents are delivered through pores formed in one cell structure targeted for agent delivery.

3. A method according to claim 1, wherein agents are delivered through pores formed in one or more cell structures targeted for agent delivery.

4. A method according to claim 1, wherein each tube is loaded with the discrete zones or bands containing agents using a microfluidic switch.

5. A method according to claim 1, wherein one or more of the electrolyte-filled tubes contain several barrels or channels.

6. A method according to claim 5, wherein the barrels or channels contain different agents.

7. A method according to claim 5, wherein each barrel or channel is individually connected to an electrode.

8. A method according to claim 1, wherein the electrical field is obtained by applying a voltage between the electrolyte filled tubes and the ground or counter electrode using a voltage generator.

9. A method according to claim 8 wherein the voltage is applied as a pulse.

10. A method according to claim 9, wherein the length of said pulse is from 0.1 µs to several minutes.

11. A method according to claim 10, wherein the length of the pulse is from 1 µs to 5 s.

12. A method according to claim 1, wherein the electrical field is obtained by applying a current between the electrolyte filled tubes and the ground or counter electrode using a current generator.

13. A method according to claim 1, wherein the electrolyte-filled tubes are electrolyte-filled capillaries.

14. A method according to 1, wherein the electrolyte-filled tubes are electrolyte-filled conically tapered tubes.

15. A method according to claim 1, wherein the electrolyte-filled tubes are electrolyte-filled electrodes.

16. A method according to claim 1, wherein the agents are introduced into the electrolyte solution contained in the electrolyte-filled tubes from the tip end of the tubes using capillary forces or aspiration or suction.

17. A method according to claim 1, wherein the agents are comprised in the electrolyte in the electrolyte-filled tubes.

18. A method according to claim 1, where the one or more cell structures targeted for agent delivery is contained in a cell bathing medium.

19. A method according to claim 1, wherein an agent is a drug.

20. A method according to claim 1, wherein the one or more cell structures targeted for agent delivery is a population of cells.

21. A method according to claim 1, wherein the one or more cell structures is a single cell.

22. A method according claim 1, wherein the one or more cell structures is a tissue.

23. A method according to claim 1, wherein the one or more cell structures is an organ.

24. A method according to claim 1, wherein the one or more cell structures is an intracellular structure.

25. A method according to claim 24, wherein the intracellular structure is an organelle.

26. A method according to claim 1, wherein the one or more cell structures targeted for agent delivery is immobilized on a surface.

27. A method according to claim 1, wherein the one or more cell structures targeted for agent delivery is contained in at least one well on a plate.

28. A method according to claim 1, wherein the one or more cell structures targeted for agent delivery has been pretreated with a genetic method prior to step (f).

29. A method according to claim 28, wherein the genetic method is a transfection method.

30. A method according to claim 1, wherein the one or more cell structures targeted for agent delivery has been pretreated with a drug prior to step (f).

31. A method according to claim 1, wherein the one or more cell structures targeted for agent delivery has been pretreated with an internalized dye or marker prior to step (d).

32. A method according to claim 1, wherein the tubes are additionally connected to a fluid delivery device.

33. A method according to claim 32, wherein the fluid delivery device is a micropump.

34. A method according to claim 32, wherein the fluid delivery device is a peristaltic pump.

35. A method according to claim 32, wherein the fluid delivery device is a gravitational pump.

36. A method according to claim 32, wherein the fluid delivery device is a pneumatic pump.

37. A method according to claim 32, wherein the fluid delivery device is a solenoid.

38. A method according to claim 32, wherein the fluid delivery device is a pressure-driven pump.

39. A method according to claim 32, wherein the fluid delivery device is used for transportation of the agents into the electrolyte-filled tubes.

40. A method according to claim 32, wherein the fluid delivery device is used for transportation of the agents into the cell structure targeted for agent delivery.

41. A method according to claim 1, wherein the one or more cell structures targeted for agent delivery is a intracellular structure and the electrolyte filled robes and the ground or counter electrode are arranged so that the ends of the robes and the ground or counter electrode are placed at a close distance to or within a host cell containing the intracellular structure.

42. A method according to claim 1, wherein the electrolyte-filled tubes are connected to a voltage generator via at least one electrode.

43. A method according to claim 1, wherein the voltage generator generates a voltage of from 10 mV to 100 V at the surface of the one or more cell structures targeted for agent delivery.

44. A method according to claim 43, wherein the voltage is from 100 mV to 10 V.

45. A method according to claim 1, wherein the electrolyte-filled tubes are connected to a current generator via at least one electrode.

46. A method according to claim 1, wherein the current needed for electroporation is carried by an intra-electrodal electrolyte present in the tubes.

47. A method according to claim 1, wherein the current needed for electroporation is carried by an electrically conductive layer on the electrolyte-filled tubes.

48. A method according to claim 1, wherein a programmed electric field with varying strength and/or wave form is used in step (f).

49. A method according to claim 1, wherein a pulsed electric field is used in step (f).

50. A method according to claim 1, wherein the close distance in step (d) is less than 100 μm.

51. A method according to claim 1, wherein the diameter of the electrolyte filled tubes at the end closest to the one or more cell structures targeted for agent delivery is from a few nanometers to a few hundred micrometers.

52. A method according to claim 1, wherein the electrolyte-filled tubes are positioned by use of a micropositioner.

53. A method according to claim 1, wherein at least one of the electrolyte-filled tubes is a hollow fused silica electrode.

54. A method according to claim 1, wherein at least one of the electrolyte-filled tubes is a polymer electrode.

55. A method according to claim 1, wherein at least one of the electrolyte-filled tubes is a fluorocarbon capillary.

56. A method according to claim 1 wherein an agent is a cell-impermeant agent.

57. A method according to claim 56, wherein the cell-impermeant agent comprise a pharmaceutically active compound.

58. A method according to claim 1, wherein an agent is an electrolyte.

59. A method according to claim 1, wherein an agent is a substance that activates receptors on the cell plasma membrane.

60. A method according to claim 1, wherein an agent is an agent that affects intracellular chemistry.

61. A method according to claim 1, wherein an agent is an agent that affects cellular physics.

62. A method according to claim 1, wherein the agents independently are selected from the group consisting of genes, RNA, DNA, colloidal particles, receptors, receptor ligands, receptor antagonists, receptor blockers, enzymes, enzyme substrates, enzyme inhibitors, enzyme modulators, proteins, amino acids, peptides, metabolites, oligonucleotides, antigens, haptens, antibodies, organelles, cell nuclei, bacteria, viruses, gametes, inorganic ions, metal ions, metal clusters, polymers, and any combinations thereof.

63. A method according to claim 1, wherein the agents are delivered into the one or more cell structures targeted for agent delivery by electrophoresis or electroosmosis.

64. A method according to claim 1, wherein the electrolyte-filled tubes are arranged in a one-dimensional array or a two-dimensional array.

65. A method according claim 64, wherein the one-dimensional array or the two-dimensional array is microfabricated from a solid substrate into a chip device, the surface of said chip device having several openings each constituted by a tip end of an individual electrolyte-filled tube.

66. A method according to claim 1, wherein each electrolyte-filled tube is individually controlled.

67. A method according to claim 66, wherein the electrolyte-filled tubes are controlled by a robotic device.

68. A method according to claim 1, wherein the electrolyte-filled tubes are population-wise controlled.

69. A method according to claim 1, wherein the one or more cell structures targeted for agent delivery can be translated in relation to the outlet ends of the electrolyte-filled tubes.

70. A method according to claim 69, wherein the one or more cell structures targeted for agent delivery is translated using a movable stage.

71. A method according to claim 70, wherein the stage is a microscope stage.

72. A method according to claim 69, wherein the one or more cell structures targeted for agent delivery is translated using a motorized stage.

73. The method according to claim 1, wherein a protein is identified.

74. The method according to claim 73, wherein the protein comprises an enzyme or a receptor for receptor identification.

75. The method according to claim 1, wherein the method is one or more of a binding assay, enzyme assay, receptor assay, viral assay, bacterial assay, drug assay, kinetic assay, pharmacokinetic assay, and pharmacology assay.

76. The method according to claim 1, wherein one or more of a metabolic pathway or a signaling pathway is modified.

77. The method according to claim 1, wherein in vitro fertilization is conducted.

78. The method according to claim 1, wherein a nucleus or organelle is transferred.

79. The method according to claim 1, wherein one or more of receptors on the surface of said one or more cell structures or receptors on the inside surface of a cell structure is screened.

80. The method according to claim 1, wherein signaling systems inside the one or more cell structures are studied.

81. The method according to claim 1, wherein the method is used in one or more of a sensor, robotics, chemical computer, or a biological computer.

82. A method according to claim 1, further comprising a step of measuring by detection of fluorescence a response evoked by an agent in one or more cell structures targeted for agent delivery, wherein the step is performed after sequentially transporting the agents through the pores and into the cytoplasm of the one or more cell structures.

83. A method according to claim 1, wherein the one or more cell structures are transfected with one or more genes, or one or more genes are identified.

* * * * *